US012593987B2

(12) United States Patent
Yu et al.

(10) Patent No.: US 12,593,987 B2
(45) Date of Patent: Apr. 7, 2026

(54) FOREHEAD TEMPERATURE MEASUREMENT SYSTEM WITH HIGH ACCURACY

(71) Applicant: PIXART IMAGING INC., Hsin-Chu County (TW)

(72) Inventors: Po-Wei Yu, Hsin-Chu County (TW); Yi-Chung Chen, Hsin-Chu County (TW); Ting-Yang Chang, Hsin-Chu County (TW); Chih-Ming Sun, Hsin-Chu County (TW); Kai-Shun Chen, Hsin-Chu County (TW); Yen-Chang Chu, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 584 days.

(21) Appl. No.: 17/385,046

(22) Filed: Jul. 26, 2021

(65) Prior Publication Data

US 2022/0061675 A1     Mar. 3, 2022

Related U.S. Application Data

(60) Provisional application No. 63/071,383, filed on Aug. 28, 2020.

(51) Int. Cl.
*A61B 5/01*          (2006.01)

(52) U.S. Cl.
CPC ...... *A61B 5/015* (2013.01); *A61B 2560/0223* (2013.01); *A61B 2560/0252* (2013.01); *A61B 2562/0271* (2013.01)

(58) Field of Classification Search
CPC ....... A61B 5/015; A61B 5/004; A61B 5/0077; A61B 5/0082; A61B 2560/0223;
(Continued)

(56) References Cited

U.S. PATENT DOCUMENTS

| | | | | |
|---|---|---|---|---|
| 2,651,237 A | * | 9/1953 | Garutso | G02B 15/00 |
| | | | | 359/740 |
| 4,998,125 A | * | 3/1991 | Watanabe | G03B 17/38 |
| | | | | 396/106 |

(Continued)

FOREIGN PATENT DOCUMENTS

| | | | | |
|---|---|---|---|---|
| CN | 102176742 A | * | 9/2011 | H04N 5/33 |
| CN | 103839218 A | * | 6/2014 | |

(Continued)

OTHER PUBLICATIONS

English Translation Chinese Patent Application Publication No. CN111537074A (Year: 2020).*

(Continued)

*Primary Examiner* — Charles A Marmor, II

*Assistant Examiner* — Andrew E Hoffpauir

(74) *Attorney, Agent, or Firm* — HAUPTMAN HAM, LLP

(57) ABSTRACT

There is provided a forehead temperature measurement system including an image sensor, a thermal sensor and a processor. The image sensor is used to output an image frame. The thermal sensor is used to output a thermal image. The processor is used to determine a forehead region in the image frame, map the forehead region to the thermal image and identify a forehead temperature according to a forehead mapped region in the thermal image. The processor further calibrates or compensates the forehead temperature according to an area of the forehead region.

19 Claims, 8 Drawing Sheets

100

(58) Field of Classification Search
CPC ..... A61B 2560/0252; A61B 2562/0271; G01J
5/0025; G01J 5/06
See application file for complete search history.

(56) References Cited

U.S. PATENT DOCUMENTS

| | | | | | |
|---|---|---|---|---|---|
| 5,687,408 A | * | 11/1997 | Park | ........................ | G03B 19/12 |
| | | | | | 396/404 |
| 5,819,007 A | * | 10/1998 | Elghazzawi | ........... | G16H 50/20 |
| | | | | | 706/924 |
| 2003/0020002 A1 | * | 1/2003 | Lee | ................... | H01L 27/14603 |
| | | | | | 348/E3.018 |
| 2004/0254472 A1 | * | 12/2004 | McQuilkin | ............ | A61B 5/015 |
| | | | | | 600/549 |
| 2005/0017946 A1 | * | 1/2005 | Park | .......................... | G06F 3/14 |
| | | | | | 345/156 |
| 2005/0146641 A1 | * | 7/2005 | Cheng | .................... | H04N 23/56 |
| | | | | | 348/E5.029 |
| 2007/0153871 A1 | * | 7/2007 | Fraden | ................... | A61B 5/015 |
| | | | | | 374/121 |
| 2007/0176213 A1 | * | 8/2007 | Oda | ................... | H01L 27/14603 |
| | | | | | 257/E27.152 |
| 2008/0278608 A1 | * | 11/2008 | Kim | ....................... | H04N 25/60 |
| | | | | | 348/E5.079 |
| 2010/0110282 A1 | * | 5/2010 | Lan | ................... | H01L 27/14625 |
| | | | | | 348/374 |

| | | | | | |
|---|---|---|---|---|---|
| 2013/0230074 A1 | * | 9/2013 | Shin | ........................ | A61B 5/01 |
| | | | | | 374/129 |
| 2014/0092939 A1 | * | 4/2014 | Chang | ..................... | G01K 7/01 |
| | | | | | 257/E23.179 |
| 2017/0209303 A1 | * | 7/2017 | Al-Anzi | .................. | A61B 5/01 |
| 2018/0092549 A1 | * | 4/2018 | Tzvieli | ................. | G06V 40/162 |
| 2019/0195694 A1 | * | 6/2019 | Tang | ........................ | G01J 5/56 |
| 2020/0068110 A1 | | 2/2020 | Guo et al. | | |
| 2021/0295517 A1 | | 9/2021 | Parrish et al. | | |
| 2021/0343005 A1 | * | 11/2021 | Kuybeda | ................. | G06T 11/60 |
| 2021/0393139 A1 | * | 12/2021 | Manneschi | .......... | A61B 5/1176 |
| 2021/0404877 A1 | * | 12/2021 | Lee | ..................... | G06V 40/171 |

FOREIGN PATENT DOCUMENTS

| | | | | | | |
|---|---|---|---|---|---|---|
| CN | | 111458039 A | * | 7/2020 | | |
| CN | | 111537074 A | * | 8/2020 | ........... | G01J 5/0025 |
| JP | | H01289390 A | * | 11/1989 | | |
| JP | | 2011159681 A | * | 8/2011 | | |

OTHER PUBLICATIONS

English Translation Chinese Patent Application Publication No. CN111458039A (Year: 2020).*
JP-2011159681-A English Translation (Year: 2011).*
CN-102176742-A English Translation (Year: 2011).*
JPH01289390A English Translation (Year: 1985).*
CN103839218 English Translation (Year: 2014).*

* cited by examiner

100

FOREHEAD TEMPERATURE MEASUREMENT SYSTEM WITH HIGH ACCURACY

CROSS REFERENCE TO RELATED APPLICATION

The present application claims the priority benefit of U.S. Provisional Application Ser. No. 63/071,383, filed on Aug. 28, 2020, the disclosure of which is hereby incorporated by reference herein in its entirety.

BACKGROUND

1. Field of the Disclosure

This disclosure generally relates to a telemetric forehead temperature measurement and, more particularly, to a forehead temperature measurement system that compensates or calibrates a forehead temperature measured by a thermal sensor so as to improve the measurement accuracy.

2. Description of the Related Art

It has become a new normal to arrange an auto forehead temperature measuring system at an entrance of the store and the building. However, different from the forehead thermometer, a distance between a measured person and the auto forehead temperature measuring system is not fixed, and a system's field of view generally covers environmental objects that could degrade the measurement accuracy. Furthermore, the fluctuated environmental temperature is also a parameter that could affect a measured temperature. Therefore, the current auto forehead temperature measuring system has a larger temperature deviation, and false alarm happens from time to time when the measured temperature is compared with a temperature threshold.

Accordingly, the present disclosure provides a forehead temperature measurement system and a temperature measuring method thereof that can compensate or calibrate the temperature deviation caused by the distance from a measured person and by the environmental temperature fluctuation.

SUMMARY

The present disclosure provides a forehead temperature measurement system including an image sensor and a thermal sensor that determines a temperature measuring range of the thermal sensor using the image sensor.

The present disclosure further provides a forehead temperature measurement system having two sets of field of view that selects a smaller field of view to improve the temperature measurement accuracy when a measured person is at a farther distance.

The present disclosure further provides a forehead temperature measurement system that calibrates a measured forehead temperature according to a ratio of a forehead region in a pixel of interest of a thermal image.

The present disclosure further provides a forehead temperature measurement system that calibrates a measured forehead temperature according to a forehead area and an environment temperature.

The present disclosure provides a forehead temperature measurement system including an image sensor, a thermal sensor and a processor. The image sensor is configured to output an image frame. The thermal sensor is configured to output a thermal image. The processor is coupled to the image sensor and the thermal sensor, and configured to recognize a forehead region and calculate a forehead area according to the image frame, map the forehead region to the thermal image to determine a mapped region, respectively determine a measured forehead temperature and an environment temperature according to temperature values inside and outside the mapped region, and calibrate the measured forehead temperature according to the forehead area and the environment temperature.

The present disclosure further provides a forehead temperature measurement system including a first image sensor, a second image sensor, a first thermal sensor and a processor. The first image sensor is configured to output a first image frame. The first thermal sensor is configured to output a first thermal image. The processor is coupled to the first image sensor, the second image sensor and the first thermal sensor, and configured to recognize a first forehead region and calculate a forehead area according to the first image frame, map the first forehead region to the first thermal image to determine a measured forehead temperature when the forehead area is larger than an area threshold, and control the second image sensor to capture a second image frame when the forehead area is smaller than the area threshold.

The present disclosure further provides a forehead temperature measurement system including a first image sensor, a first thermal sensor and a processor. The first image sensor is configured to output a first image frame. The first thermal sensor is configured to output a first thermal image. The processor is coupled to the first image sensor and the first thermal sensor, and configured to recognize a forehead region according to the first image frame, map the forehead region to the first thermal image to determine a mapped region, determine an environment temperature according to a temperature value outside the mapped region, find a pixel of interest which has a maximum temperature inside the mapped region, and recognize a ratio of the forehead region in a corresponding region in the first image frame corresponding to the pixel of interest, and calculate a measured forehead temperature according to the maximum temperature, the ratio and the environment temperature when the ratio is lower than a ratio threshold.

The present disclosure further provides a forehead temperature measurement system including an image sensor, a thermal sensor and a processor. The image sensor is configured to output an image frame. The thermal sensor is configured to output a thermal image. The processor is coupled to the image sensor and the thermal sensor, and configured to recognize a forehead region according to the image frame, map the forehead region to the thermal image to determine a mapped region, determine a maximum temperature inside the mapped region as a measured forehead temperature, and calibrate the measured forehead temperature according to uniformity of temperature differences between the measured forehead temperature and adjacent temperatures of the measured forehead temperature.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

The forehead temperature measurement system of the present disclosure firstly determines a forehead region in an image frame captured by an image sensor using the image recognition technique, and then determines a measured forehead temperature according to a mapped region, corresponding to the forehead region, in a thermal image captured by a thermal sensor. Furthermore, the forehead temperature measurement system of the present disclosure further compensates or calibrates the measured forehead temperature according to an area of the forehead region so as to improve the measurement accuracy.

Figure 1:
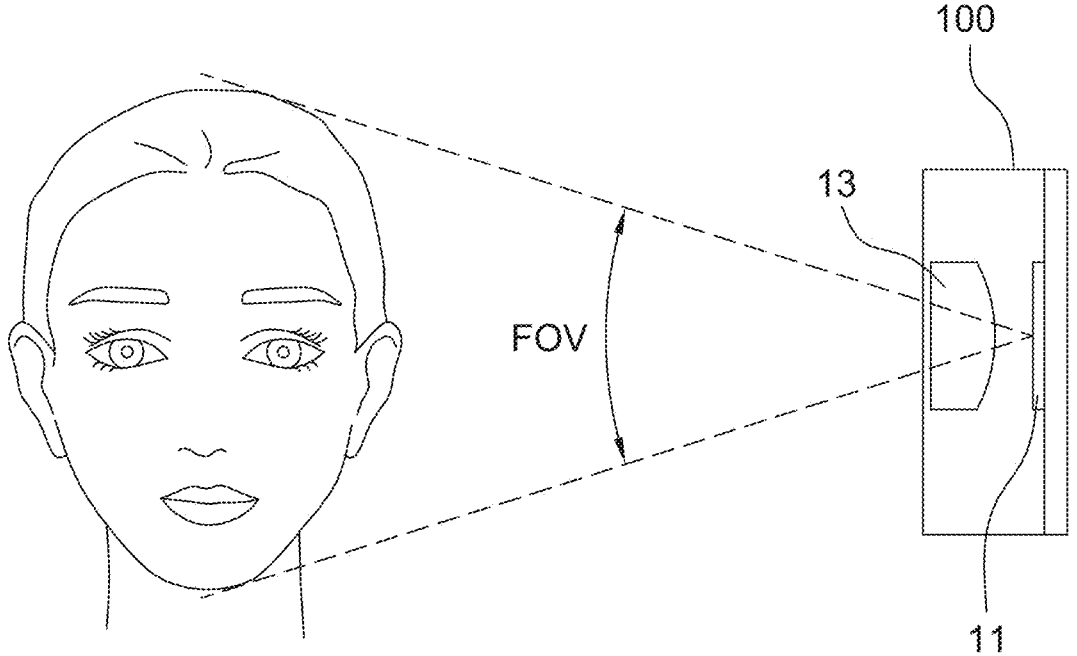
FIG. 1 is an operational schematic diagram of a forehead temperature measurement system according to one embodiment of the present disclosure.
Figure 2:
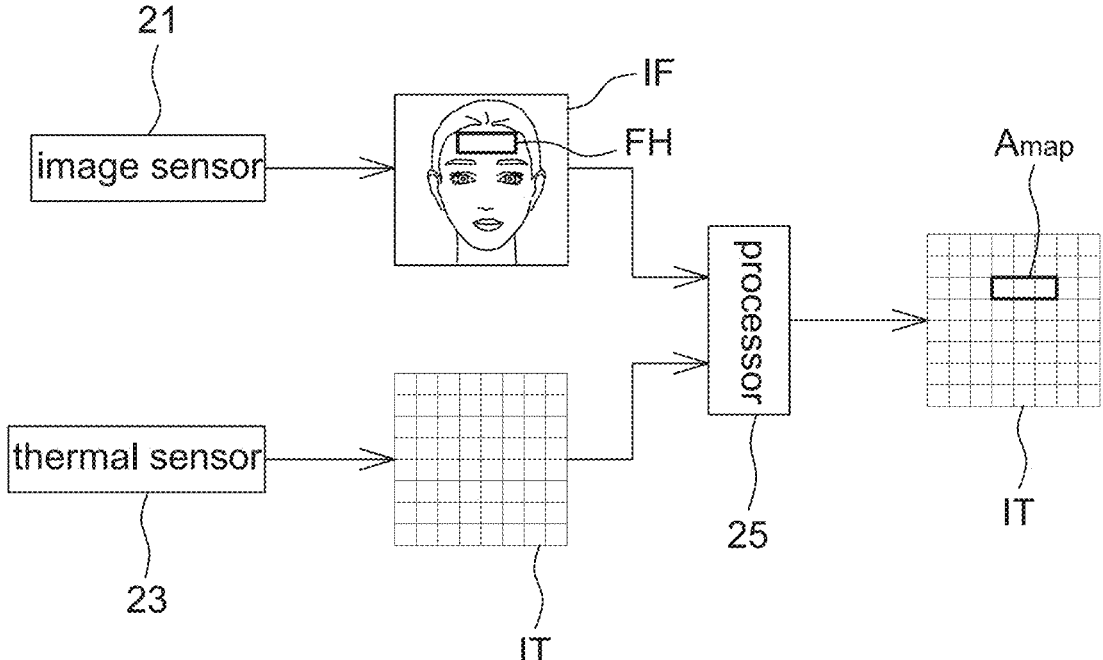
FIG. 2 is a schematic block diagram of a forehead temperature measurement system according to one embodiment of the present disclosure.

Please refer to FIGS. 1 and 2, FIG. 1 is an operational schematic diagram of a forehead temperature measurement system 100 according to one embodiment of the present disclosure, and FIG. 2 is a schematic block diagram of a forehead temperature measurement system 100 according to one embodiment of the present disclosure.

The forehead temperature measurement system 100 includes a sensing chip 11 and a lens 13, wherein the lens 13 is arranged at a side of the sensing chip 11 for receiving light so as to adjust the light path and field of view FOV.

The sensing chip 11 includes an image sensor 21, a thermal sensor 23 and a processor 25. The image sensor 21 and the thermal sensor 23 both receive optical energy via the lens 13. The sensing chip 11 is coupled to external devices via a substrate on which the sensing chip 11 is arranged.

The image sensor 21 (and 21' if included) is, for example, a CCD image sensor or a CMOS image sensor, and is used to output an image frame IF at a predetermined frequency. For example, FIG. 2 shows that the image frame IF contains a human face image. The thermal sensor 23 (and 23' if included) is a far infrared sensor, and is used to sense far infrared light generated by a human body to output, corresponding, to capturing of the image frame IF, a thermal image IT.

In one aspect, the image sensor 21 and the thermal sensor 23 have an identical field of view FOV so as to receive optical energy from the same space, but the present disclosure is not limited thereto. In another aspect, the FOV of the image sensor 21 is larger than or smaller than that of the thermal sensor 23.

In one aspect, a pixel number of the image frame IF is higher than a pixel number of the thermal image IT. The image frame IF includes, for example, 240×240 pixels so as to contain enough details or features for the processor 25 to perform the image recognition, e.g., including face recognition and recognizing a forehead region of a face. The thermal image IT includes, for example, 8×8 pixels so as to detect temperatures of 64 points within the FOV.

The processor 25 is coupled to the image sensor 21 and the thermal sensor 23 to respectively receive the image frame IF and the thermal image IT. The processor 25 is, for example, a digital signal processor (DSP), an application specific integrated circuit (ASIC) or a field programmable gate array (FPGA), and implements functions thereof using hardware and/or firmware. Said functions include recognizing a forehead region FH and calculating a forehead area according to the image frame IF, mapping the forehead region FH to the thermal image IT to determine a mapped region $A_{map}$, determining a measured forehead temperature according to a temperature value inside the mapped region $A_{map}$, and compensating or calibrating the measured forehead temperature using the method mentioned below.

The mapping of the forehead region FH is illustrated by examples below.

In one example, the thermal image IT is interpolated to form an interpolated thermal image having the same number of pixels as the image frame IF, and a corresponding mapped region $A_{map}$ in the interpolated thermal image is obtained by overlapping the image frame IF on the interpolated thermal image.

In another example, one pixel of the thermal image IT (e.g., one rectangle in FIG. 2) is corresponded to multiple pixels of the image frame IF, e.g., based on the assumption above one pixel of the thermal image IT corresponding to 30×30 pixels of the image frame IF, and thus it is able to obtain the mapped region $A_{map}$ in the thermal image IT. Based on this assumption, if the mapped region $A_{map}$ includes one pixel of the thermal image IT, the mapped region $A_{map}$ covers corresponding 30×30 pixels of the image frame IF, and so on.

In one aspect, the measured forehead temperature is the maximum temperature inside the mapped region $A_{map}$ of the thermal image IT, but the present disclosure is not limited thereto. In another aspect, the measured forehead temperature is an average of multiple measured temperature values inside the mapped region $A_{map}$ of the thermal image IT. One pixel of the thermal image IT detects one measured temperature value.

To improve the measurement accuracy, the forehead temperature measurement system 100 of the present disclosure further calibrates or compensates the measured forehead temperature. That is, the measured temperature value of a pixel outside the mapped region $A_{map}$ of the thermal image IT is not used as the measured forehead temperature but is used to compensate or calibrate the measured forehead temperature.

Figure 3:
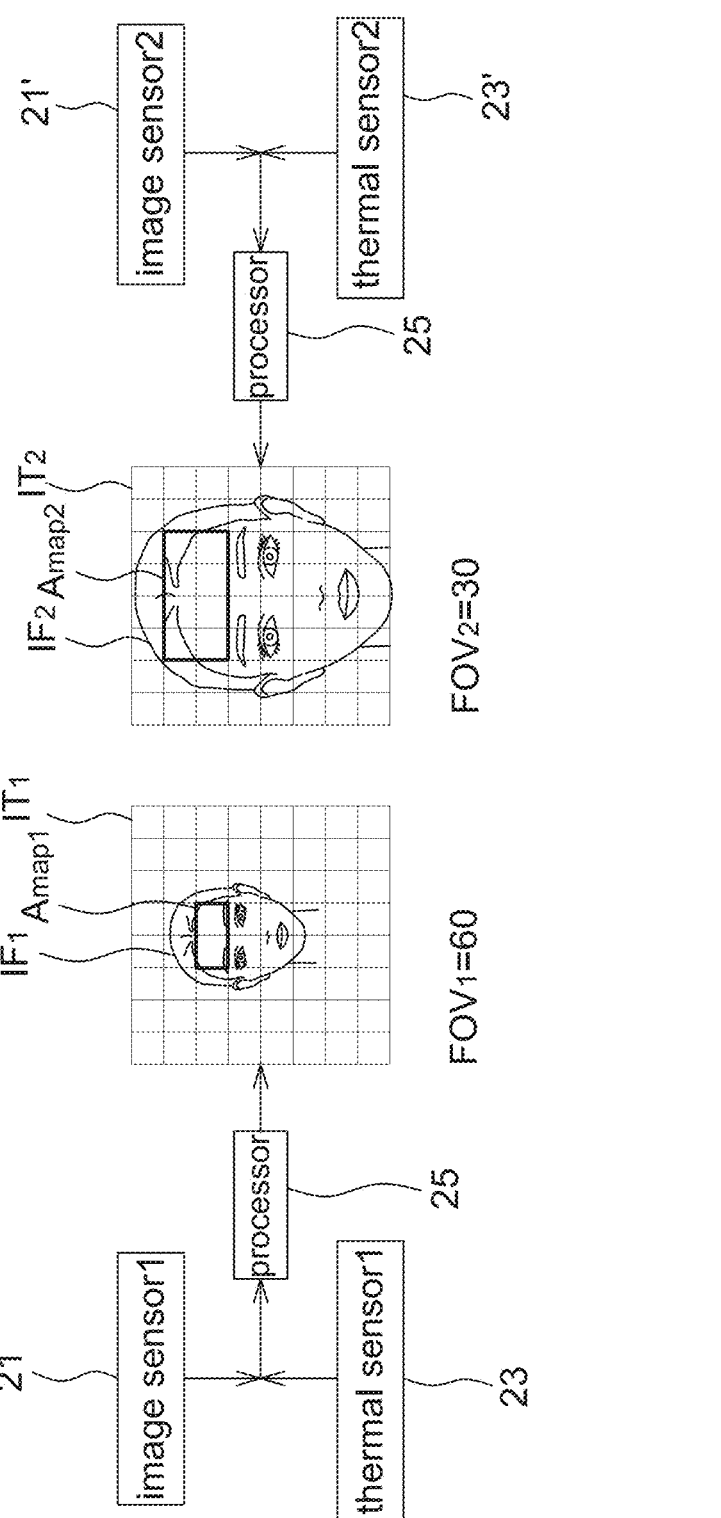
FIG. 3 is a schematic diagram of the temperature measuring of a forehead temperature measurement system according to one embodiment of the present disclosure.

Please refer to FIG. 3, it is a schematic diagram of the temperature measuring of a forehead temperature measurement system 100 according to one embodiment of the present disclosure. In this embodiment, in addition to the image sensor (or referred to first image sensor) 21 and the thermal sensor (or referred to first thermal sensor) 23, the forehead temperature measurement system 100 further includes an image sensor (or referred to second image sensor) 21' and a thermal sensor (or referred to second thermal sensor) 23', wherein the second image sensor 21' and the second thermal sensor 23' are also coupled to the processor 25.

It should be mentioned that although FIG. 3 shows two processors 25, they are only intended to illustrate the operation of two conditions (or modes). The temperature measurement system 100 uses one processor 25 to execute all functions as mentioned above.

In one aspect, the first image sensor 21 and the first thermal sensor 23 have a first field of view, e.g., $FOV_1=60$. The second image sensor 21' and the second thermal sensor 23' have a second field of view, e.g., $FOV_2=30$.

The first image sensor 21 outputs a first image frame $IF_1$, e.g., shown by a human face image when $FOV_1=60$. The first thermal sensor 23 outputs a first thermal image $IT_1$, e.g., shown by a pixel array including 8×8 pixels. The second image sensor 21' outputs a second image frame $IF_2$, e.g., shown by a human face image when $FOV_2=30$. The second thermal sensor 23' outputs a second thermal image $IT_2$, e.g., shown by a pixel array including 8×8 pixels. FIG. 3 shows an overlap of the first image frame $IF_1$ and the first thermal image $IT_1$, and an overlap of the second image frame $IF_2$ and the second thermal image $IT_2$, and said overlap is performed by the processor 25.

More specifically, the processor 25 recognizes a first forehead region (e.g., FH as shown in FIG. 2) and calculates a forehead area according to the first image frame $IF_1$. When the forehead area is larger than an area threshold (e.g., recorded in a memory), the processor 25 maps the first forehead region to the first thermal image $IT_1$ to accordingly determine a measured forehead temperature, including mapping the first forehead region FH to the first thermal image $IT_1$ to determine a first mapped region and then determining the measured forehead temperature according to a temperature value inside the first mapped region $A_{map1}$. As mentioned above, the measured forehead temperature is the maximum temperature or an average temperature inside the first mapped region $A_{map1}$.

When the forehead area is smaller than the area threshold, the processor 25 controls the second image sensor 21' to capture a second image frame $IF_2$, recognizes a second forehead region according to the second image frame $IF_2$, maps the second forehead region to a second thermal image $IT_2$ captured by the second thermal sensor 23' to determine a second mapped region $A_{map2}$, and determines a measured forehead temperature according to a temperature value inside the second mapped region $A_{map2}$.

In FIG. 3, the processor 25 obtains a measured forehead temperature according to the first mapped region $A_{map1}$ or the second mapped region $A_{map2}$ by using the method identical to FIG. 2, only different sets of sensors being used to perform the calculation. In the embodiment of FIG. 3, when a human face image in the first image frame $IF_1$ is too small (e.g., forehead area smaller than area threshold), the measured forehead temperature is determined by using the second image sensor 21' and the second thermal sensor 23'. Because the second image sensor 21' and the second thermal sensor 23' have a smaller FOV, the human face occupies a larger region in the FOV such that higher measurement accuracy is obtained. For example, the processor 25 is arranged not to process the first thermal image $IT_1$ when the forehead area is smaller than the area threshold, but is arranged to determine the measured forehead temperature according to the first image frame $IF_1$ and the first thermal image $IT_1$ only when the forehead area is larger than or equal to the area threshold.

If the processor 25 needs to calibrate the measured forehead temperature calculated from the second image frame $IF_2$ and the second thermal sensor $IT_2$ using the method mentioned below, the processor 25 further calculates a forehead area according to the second image frame $IF_2$ and an environment temperature according to the second thermal sensor $IT_2$.

Figure 4:
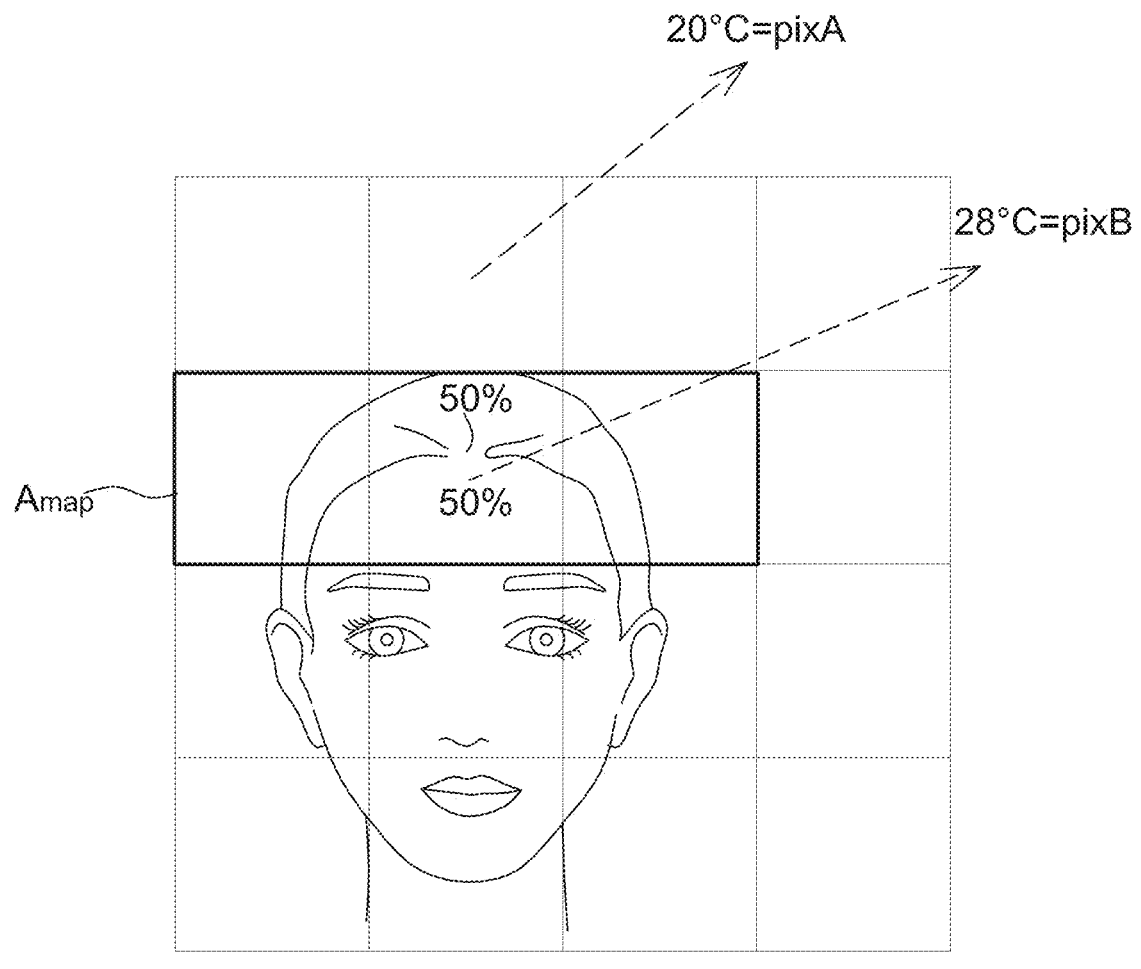
FIG. 4 is another schematic diagram of the temperature measuring of a forehead temperature measurement system according to one embodiment of the present disclosure.

Please refer to FIG. 4, it is another schematic diagram of the temperature measuring of a forehead temperature measurement system 100 according to one embodiment of the present disclosure. Please refer to FIG. 2 together, after receiving the image frame IF and the thermal image IT, the processor 25 recognizes a forehead region FIT according to the image frame IF, maps the forehead region FH to the thermal image IT to determine a mapped region $A_{map}$, determines an environment temperature according to a temperature value outside (e.g., pixA in FIG. 4) the mapped region $A_{map}$, finds a pixel of interest (e.g., pixB in FIG. 4) having a maximum temperature inside the mapped region $A_{map}$, recognizes a ratio (e.g., FIG. 4 showing 50% forehead and 50% non-forehead) of the forehead region FH in a corresponding region in the image frame IF corresponding to the pixel of interest pixB, and calculates a measured forehead temperature according to the maximum temperature, the ratio and the environment temperature when the ratio is smaller than a ratio threshold (e.g., 90% to 95% stored in the memory).

In one aspect, the environment temperature is a measured temperature value, e.g., shown as 20° C. in FIG. 4, of a pixel pixA adjacent to the pixel of interest pixB having the maximum temperature (e.g., shown as 28° C. in FIG. 4) in the thermal image IT. The processor 25 recognizes a ratio of forehead region and non-forehead region in a pixel region (e.g., having 30×30 pixels) of the image frame IF corresponding to the pixel of interest pixB. For example, a measured forehead temperature is assumed to be X, and the measured forehead temperature X=36° C. is obtained according to an equation X*50%+20*50%=28. That is, after the ratio of areas of forehead region and non-forehead region, the environment temperature and the maximum temperature are obtained, the corresponding measured forehead temperature is then obtained. In the present disclosure, the measured forehead temperature is not directly equal to the measured temperature value of the pixel of interest.

It is appreciated that the environment temperature is not limited to the measured temperature value of pixA in FIG. 4 but is a measured temperature value of other pixels outside the mapped region $A_{map}$.

However, when the ratio is higher than the ratio threshold, the influence from the environment temperature is considered ignorable, and the processor 25 takes the maximum temperature of the pixel of interest pixB as the measured forehead temperature.

Furthermore, the temperature measuring of FIG. 4 is combinable to the temperature measuring of FIG. 3 (i.e. including two sets of image sensor and thermal sensor). That is, the processor 25 calculates a forehead area according to a first image frame (e.g., $IF_1$ shown in FIG. 3) acquired by the first image sensor 21; and when the forehead area is larger than an area threshold, the processor 25 calculates a measured forehead temperature according to the first image frame $IF_1$ and a thermal image (e.g., $IT_1$ shown in FIG. 3) acquired by the first thermal sensor 23 based on the descriptions of FIG. 4. When the calculated forehead area is smaller than the area threshold, the processor 25 controls the second image sensor 21' to acquire a second image frame (e.g., $IF_2$ shown in FIG. 3) to replace the first image frame $IF_1$ and controls the second thermal sensor 23' to acquire a second thermal image (e.g., $IT_2$ shown in FIG. 3) to replace the first thermal image $IT_1$, and then calculates a measured forehead temperature according to the second image frame $IF_2$ and the second thermal image $IT_2$ based on the descriptions of FIG. 4.

Figure 5:
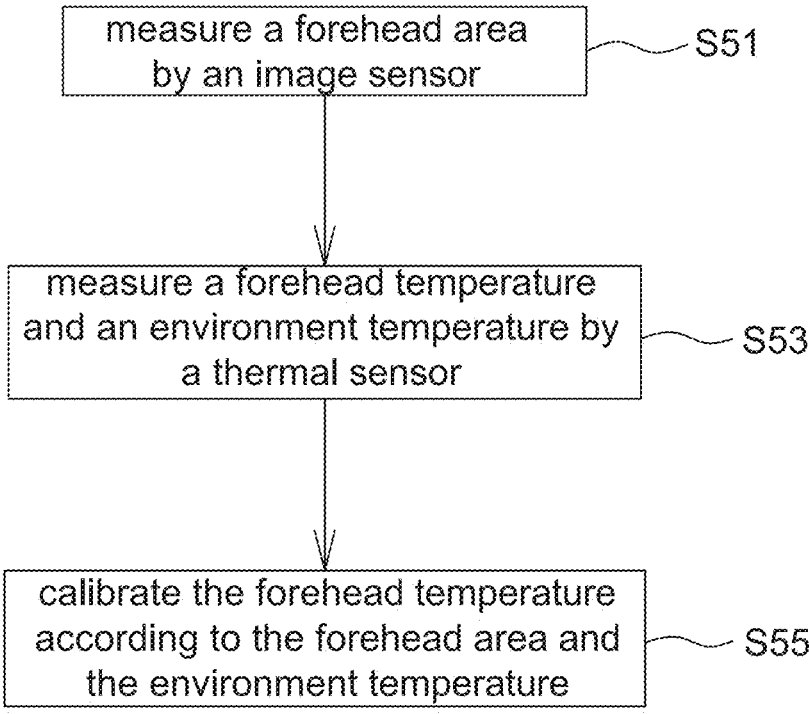
FIG. 5 is a flow chart of a temperature measuring method of a forehead temperature measurement system according to one embodiment of the present disclosure.

Please refer to FIG. 5, it is a flow chart of a temperature measurement method of a forehead temperature measurement system 100 according to one embodiment of the present disclosure, including the steps of: measuring a forehead area using an image sensor (Step S51); measuring a forehead temperature and an environment temperature using a thermal sensor (Step S53); and calibrating the forehead temperature according to the forehead area and the environment temperature (Step S55).

Please refer to FIG. 2 together, one aspect of a temperature measurement method is described below.

Step S51: After receiving the image frame IF, the processor 25 recognizes a forehead region FH in the image frame IF and calculates a forehead area of the forehead region FH. For example, the processor 25 is embedded with an image recognition algorithm (e.g., a model constructed using AI algorithm, but not limited to) for recognizing the forehead region FH. The processor 25 further calculates a number of pixels in the image frame IF occupied by the forehead region FH as a forehead area.

Step S53: After receiving the thermal image IT, the processor 25 then maps the forehead region FH to the thermal image IT to determine a mapped region $A_{map}$ in the thermal image IT. The processor 25 takes a maximum temperature or an average temperature inside the mapped region $A_{map}$ as a measured forehead temperature, and takes a temperature value outside the mapped region $A_{map}$ (e.g., a measured temperature value of a pixel adjacent to the mapped region $A_{map}$ or an averaged measured temperature values of multiple pixels adjacent to the mapped region $A_{map}$) as an environment temperature.

Step S55: Finally, the processor 25 calibrates the measured forehead temperature according to the forehead area and the environment temperature. For example, when the forehead area is smaller, a calibration for calibrating the forehead temperature is larger. For example, when the environment temperature is lower, a calibration for calibrating the forehead temperature is larger. The calibration is, for example, a temperature increment to cause the calibrated forehead temperature to be higher than the measured forehead temperature. In one aspect, when the forehead area is larger than or equal to a predetermined area, the calibration associated with the forehead area is reduced to 0. In another aspect, when the environment temperature is larger than or equal to a predetermined temperature, the calibration associated with the environment temperature is reduced to 0.

Therefore, the forehead temperature measurement system 100 of the present disclosure further includes a memory for previously storing the corresponding relationship between the forehead area and the environment temperature as well as calibrations of the measured forehead temperature such that the processor 25 determines a current calibration according to a current forehead area and a current environment temperature based on the corresponding relationship. The processor 25 then adds the current calibration to a current measured forehead temperature to obtain a calibrated forehead temperature.

In one aspect, before shipment, the forehead temperature measurement system 100 is used to measure a user to calculate measured forehead temperatures under different forehead areas (e.g., corresponding to different distances)

and different environment temperatures. Reference temperatures of the same user under the same conditions are obtained by using an accurate temperature sensor (e.g., forehead thermosensor or contact temperature sensor). Then, the forehead area and the environment temperature are used as variables, and the measured forehead temperatures are fitted to the reference temperatures using the fitting method to obtain a fitted equation to be recorded in the memory.

The corresponding relationship is not limited to be obtained using the fitting method as long as the recorded relationship can calibrate the measured forehead temperatures corresponding to different forehead areas and environment temperatures to be close to or even equal to the reference temperatures (i.e. obtaining the calibrations corresponding to different forehead areas and environment temperatures).

Similarly, the embodiment of FIG. 5 is also combinable with the embodiment of FIG. 3. When identifying that the forehead area is smaller than an area threshold, the processor 25 controls the set of sensors having a smaller FOV to perform the forehead temperature measuring. When identifying that the forehead area is larger than or equal to the area threshold, the processor 25 controls the set of sensors having a larger FOV to perform the forehead temperature measuring.

Figure 6:
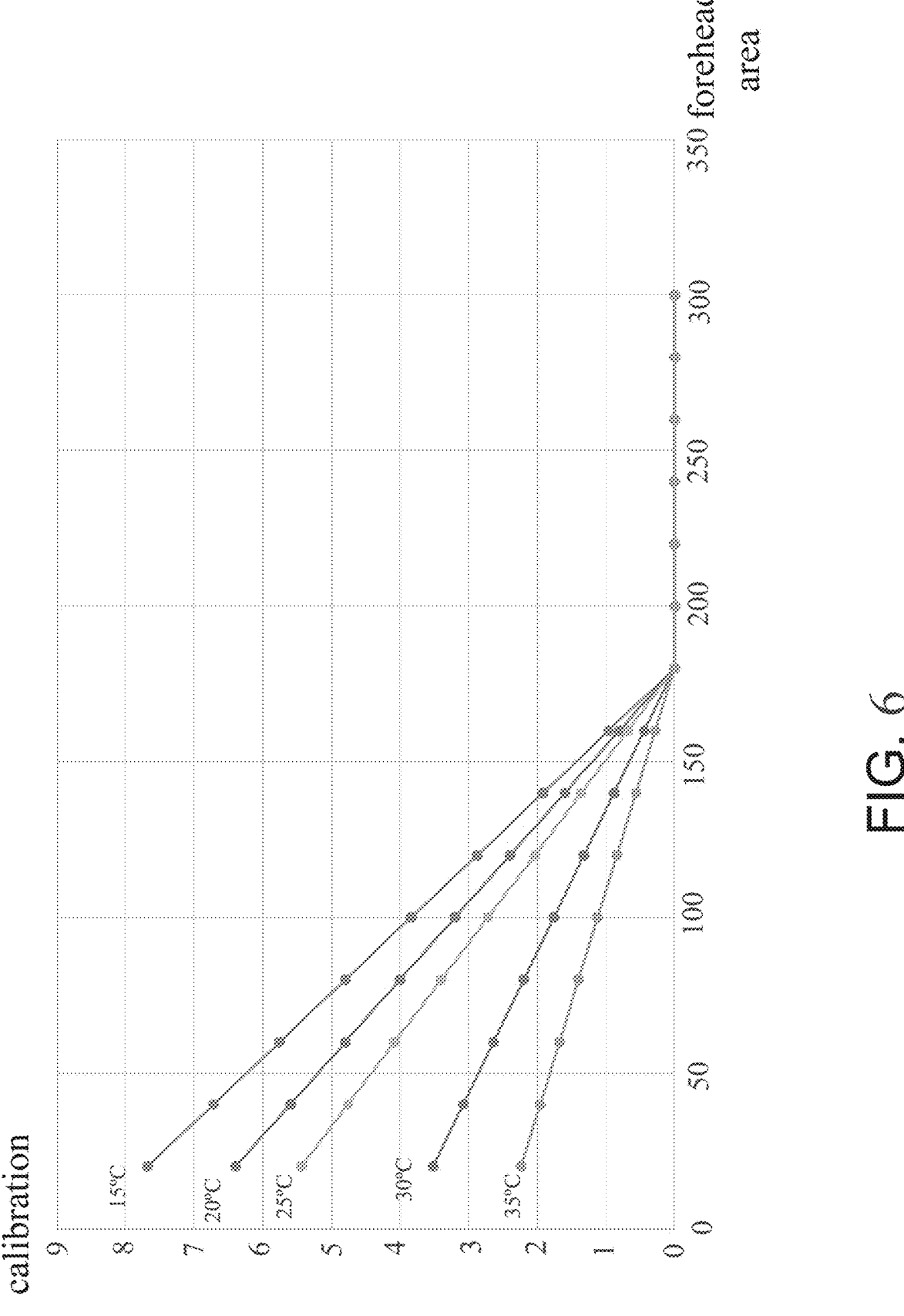
FIG. 6 is a schematic diagram of the temperature compensation of a forehead temperature measurement system according to one embodiment of the present disclosure.

Please refer to FIG. 6, it shows calibrations corresponding to different forehead areas and environment temperatures, wherein a unit of the vertical axis is $^\circ$ C. When the environment temperature (e.g., shown as 15$^\circ$ C. 20$^\circ$ C., 25$^\circ$ C., 30$^\circ$ C. and 35$^\circ$ C., but not limited to) is lower, the current measured forehead temperature is compensated by a larger calibration corresponding to the same forehead area (e.g., shown as 50, 100, 150, 200, 250 and 300, but not limited to).

Figure 7:
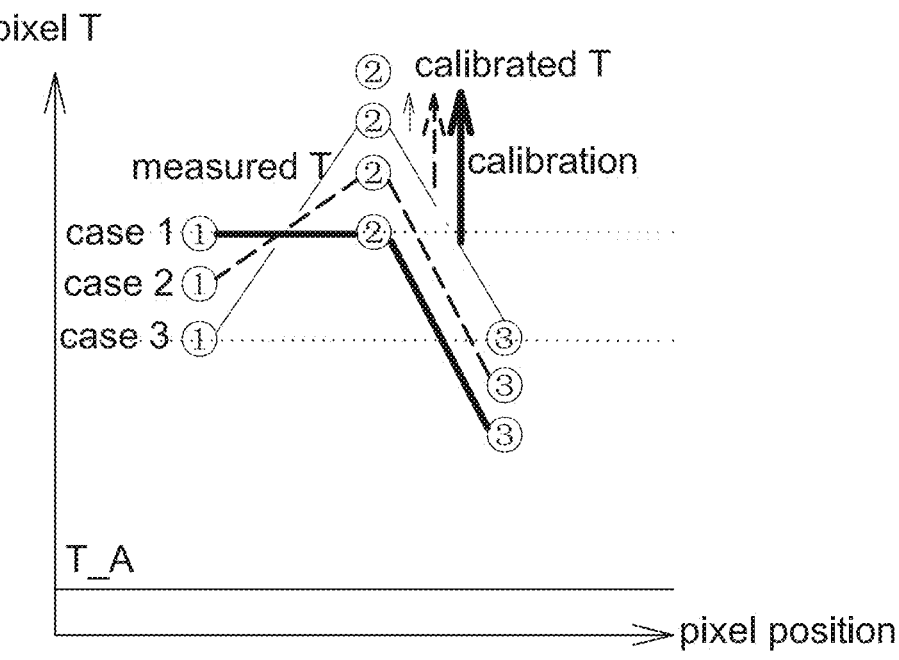
FIG. 7 is a schematic diagram of the temperature compensation of a forehead temperature measurement system according to another embodiment of the present disclosure.

Please refer to FIG. 7, it is a schematic diagram of a temperature measurement method of a forehead temperature measurement system 100 according to one embodiment of the present disclosure, including the steps of: measuring a forehead area using an image sensor measuring a forehead temperature and adjacent temperatures using a thermal sensor; and calibrating the forehead temperature according to the forehead temperature and the adjacent temperatures.

Please refer to FIG. 2 together, one aspect of a temperature compensation method is described below.

After receiving the image frame IF, the processor 25 recognizes a forehead region 1111 in the image frame IF and calculates a forehead area of the forehead region FH. For example, the processor 25 is embedded with an image recognition algorithm (e.g., a model constructed using AI algorithm, but not limited to) for recognizing the forehead region FH. The processor 25 further calculates a number of pixels in the image frame IF occupied by the forehead region FH as the forehead area.

After receiving the thermal image IT, the processor 25 then maps the forehead region FH to the thermal image IT to determine a mapped region $A_{map}$ in the thermal image IT. The processor 25 takes a maximum temperature inside the mapped region $A_{map}$ as a measured forehead temperature, and takes temperature values adjacent to a pixel associated with the measured forehead temperature as the adjacent pixels. As shown in FIG. 7, it is assumed that the mapped region $A_{map}$ includes 3 pixels (or 3 pixel regions each including multiple pixels), and a middle pixel (e.g., indicated as ②) outputs the measured forehead temperature and adjacent pixels (e.g., indicated as ① and ③) output adjacent temperatures. It is appreciated that the mapped region $A_{map}$ is not limited to include 3 pixels or pixel regions.

In one aspect, the temperature compensation of this aspect is performed only when the processor 25 identifies that the forehead area is smaller than a predetermined area threshold. When the forehead area is larger than or equal to the predetermined area threshold, the measured forehead temperature is directed outputted without compensation.

Finally, the processor 25 calibrates the measured forehead temperature according to the measured forehead temperature and the adjacent temperatures. For example in a scenario that the mapped region $A_{map}$ includes 3 pixels, the processor 25 firstly calculates a first temperature difference and a second temperature difference between the measured forehead temperature and two adjacent temperatures (e.g., including a first adjacent temperature and a second adjacent temperature), and then calibrates the measured forehead temperature according to uniformity of the first temperature difference and the second temperature difference.

Figure 8A:
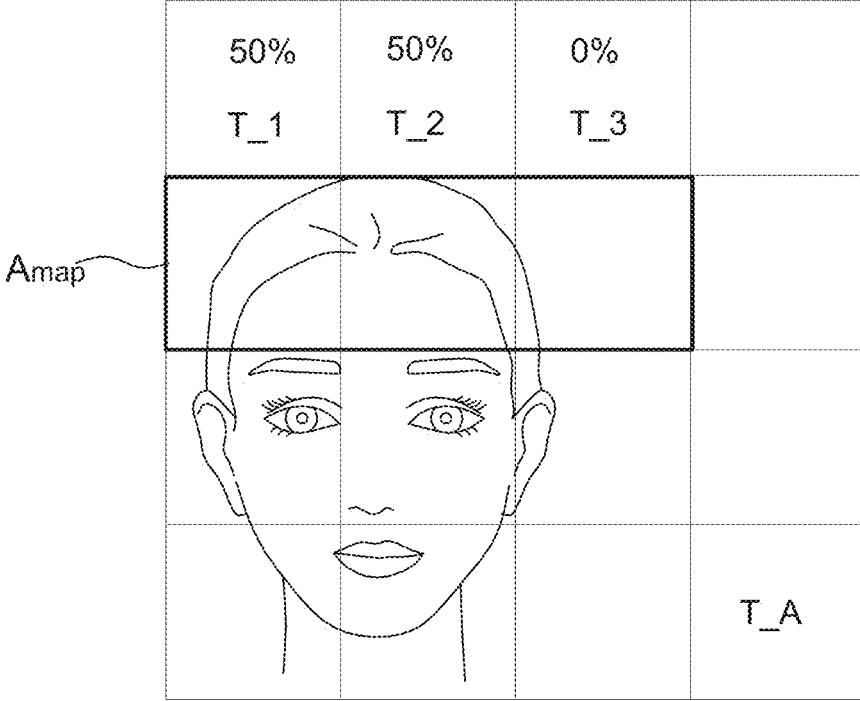
FIGS. 8A to 8C are schematic diagrams of the temperature compensation of FIG. 7.

Please refer to FIGS. 7 and 8A together, the case 1 shows that the measured forehead temperature is T_2, the first adjacent temperature is T_1 and the second adjacent temperature is T_2. In FIG. 8A, a forehead region is mainly corresponding to pixels having T_1 and T_2, and T_1 is substantially identical to T_2. The pixel having T_3 is outside the forehead region and thus has the lowest temperature. In this case, the first temperature difference (T_2−T_1) is substantially identical to 0, and the second temperature difference (T_2−T_3) is large. The uniformity of case 1 is low, and thus the processor 25 determines a larger calibration value.

Figure 8B:
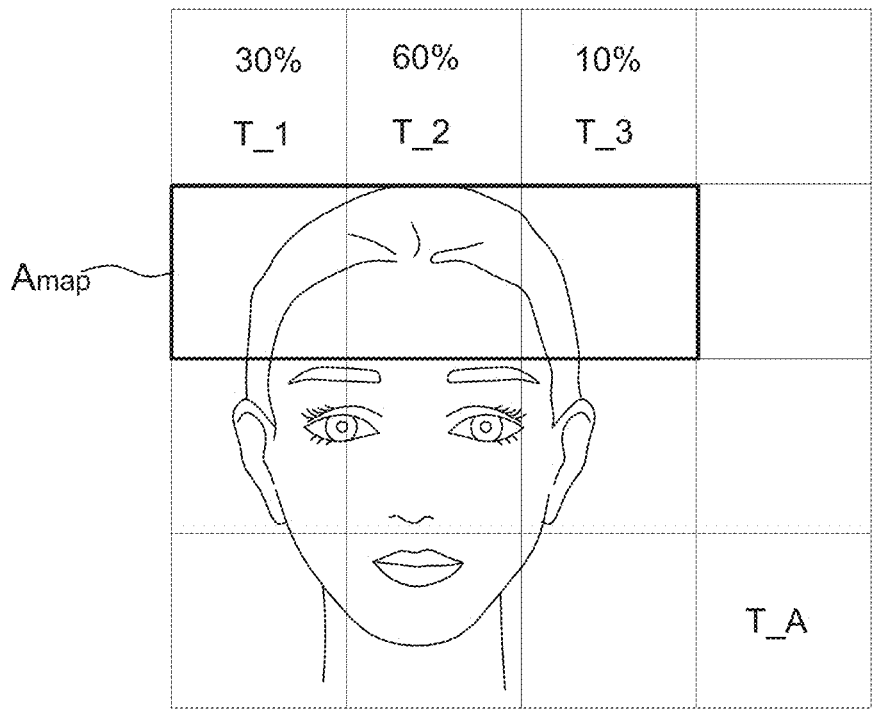

Please refer to FIGS. 7 and 8B together, the case 2 shows that the pixel having T_2 is corresponding to the maximum forehead region (e.g., 60%), and the pixel having T_3 is corresponding to the minimum forehead region (e.g., 10%). In this case, the first temperature difference is smaller than the second temperature difference, which is smaller than the second temperature difference in FIG. 8A. Accordingly, the case 2 has a higher uniformity than case 1, and thus the processor 25 determines a smaller calibration value than case 1.

Figure 8C:
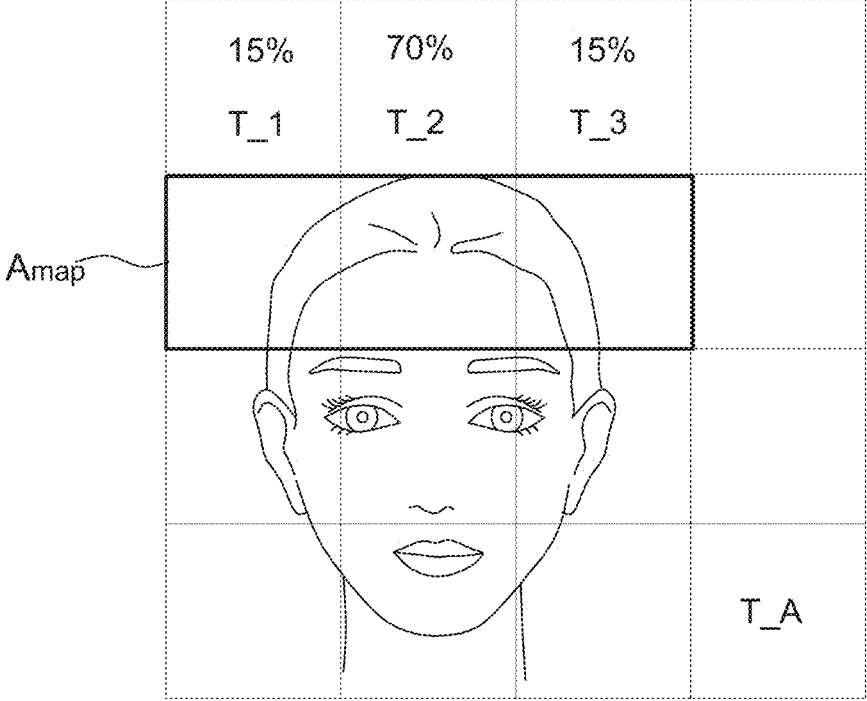

Please refer to FIGS. 7 and 8C together, the case 3 shows that the pixel having T_2 is corresponding to the maximum forehead region (e.g., 70%), and pixels having T_1 and T_3 are corresponding to smaller and identical forehead regions (e.g., 15%). In this case, the first temperature difference is substantially identical to the second temperature difference. The uniformity of case 3 is higher, and thus the processor 25 determines a smaller calibration value.

In other words, if the uniformity is lower (e.g., case 1), the calibration is larger (i.e. more temperature being added to the measured forehead temperature); otherwise, if the uniformity is higher (e.g., case 3), the calibration is smaller (i.e. less temperature being added to the measured forehead temperature).

The forehead temperature measurement system 100 of the present disclosure further includes a memory for previously storing the corresponding relationship between the uniformity and calibrations of the measured forehead temperature such that the processor 25 determines a current calibration according to a current measured forehead temperature and current adjacent temperatures based on the corresponding relationship. The processor 25 then adds the current calibration to the current measured forehead temperature (measured T shown in FIG. 7) to obtain a calibrated forehead temperature (calibrated T shown in FIG. 7).

In one aspect, before shipment, the forehead temperature measurement system 100 is used to measure a user to calculate uniformity under different measured forehead temperatures and adjacent temperatures. Reference temperatures of the same user under the same conditions are obtained by using an accurate temperature sensor e.g., forehead thermosensor or contact temperature sensor). Then, the measured forehead temperature and the adjacent temperature are used as variables, and the measured forehead temperatures are fitted to the reference temperatures using the fitting method to obtain a fitted equation to be recorded in the memory.

The corresponding relationship is not limited to be obtained using the fitting method as long as the recorded relationship can calibrate the measured forehead temperatures corresponding to different measured forehead temperatures and adjacent temperatures (or uniformity) to be close to or even equal to the reference temperatures (i.e. obtaining the calibrations corresponding to different uniformity).

Similarly, the embodiment of FIG. 7 is also combinable with the embodiment of FIG. 3. When identifying that the forehead area is smaller than an area threshold, the processor 25 controls the set of sensors having a smaller FOV to perform the forehead temperature measuring. When identifying that the forehead area is larger than or equal to the area threshold, the processor 25 controls the set of sensors having a larger FOV to perform the forehead temperature measuring.

Furthermore, the embodiment of FIG. 7 is also combinable with the embodiment of FIG. 5. That is, the processor 25 compensates a measured forehead temperature according to the forehead area, the environment temperature and the distribution of adjacent temperatures in the mapped region $A_{map}$ (e.g., uniformity).

In the present disclosure, the measured forehead temperature or the calibrated forehead temperature is outputted to a display to be shown thereon and/or compared with a temperature threshold to determine whether to generate a warning. For example, the forehead temperature measurement system 100 is arranged to directly output the measured forehead temperature or the calibrated forehead temperature, or to output a flag signal (e.g., outputting digital value 1 when the forehead temperature exceeds 38° C., but not limited to) to indicate that the body temperature is too high.

It should be mentioned that the values mentioned in the above embodiments and drawings, e.g., including temperatures, FOVs, area ratios and pixel numbers are only intended to illustrate but not to limit the present disclosure.

In the present disclosure, the forehead area is, for example, a length, a width or length×width of the forehead region FH.

It should be mentioned that although the above embodiments are illustrated in the way that a forehead area is calculated by the processor 25 according to the image frame IF, e.g., a pixel number of the forehead region FH in the image frame IF, the present disclosure is not limited thereto. In another aspect, the processor 25 calculates the forehead area according to the mapped region $A_{map}$ in the thermal image IT, e.g., a number of pixels of the mapped region $A_{map}$ in the thermal image IT.

As mentioned above, the conventional auto forehead temperature measuring system suffers from a temperature deviation caused by the distance of a measured person and the fluctuation of environment temperature. Accordingly, the present disclosure further provides a forehead temperature measurement system capable of compensating or calibrating a measured forehead temperature (e.g., FIGS. 1-4) and a temperature measuring method thereof (e.g., FIG. 5) that firstly confirm a forehead region using an image frame and then determine a measured forehead temperature according to a corresponding region in a thermal region corresponding to the forehead region. Finally, the measured forehead temperature is compensated or calibrated according to a forehead area of the forehead region so as to improve the measurement accuracy.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A forehead temperature measurement system, configured to measure a forehead temperature of a person at a distance, comprising:

a substrate;

a lens; and a sensing chip, arranged on the substrate, and comprising:

an image sensor, comprising a first pixel array having a first number of pixels and having a first field of view configured to cover a face of the person during an operation to receive optical energy from the face via the lens to output an image frame having the first number of pixels;

a thermal sensor, comprising a second pixel array having a second number of pixels and having a second field of view configured to cover the face of the person during the operation to receive far infrared light from the face via the lens to output a thermal image having the second number of pixels, which is smaller than the first number of pixels;

a processor, coupled to the image sensor and the thermal sensor, and configured to recognize a forehead region and calculate a forehead area according to the image frame, interpolate the thermal image to cause the second number of pixels to become the first number of pixels to form an interpolated thermal image, map a pixel range of the forehead region in the image frame to the interpolated thermal image, by overlapping the first number of pixels of the image frame on the first number of pixels of the interpolated thermal image, to determine a mapped region as a determined temperature measuring range of the thermal sensor, determine a measured forehead temperature according to a temperature value inside the mapped region in the interpolated thermal image, determine an environment temperature according to a temperature value of a pixel in the interpolated thermal image, wherein the pixel is outside and directly adjacent to the mapped region of the forehead region, calibrate the measured forehead temperature according to a size of the forehead area and the environment temperature determined from the interpolated thermal image to cause the forehead temperature measurement system to be adapted to different distances to compensate for a temperature deviation caused by the distance from the person and environmental temperature fluctuation in a telemetric forehead temperature measurement to prevent a false alarm from happening, output a digital value as a flag signal upon the calibrated forehead temperature being higher than a predetermined temperature, and output the calibrated forehead temperature; and a display, configured to receive the calibrated forehead temperature and show the received calibrated forehead temperature thereon, and receive the flag signal and generate a warning indicating that a body temperature of the person is too high, wherein the first number of pixels is arranged to have a sufficient number to cause the image frame to contain sufficient details for the processor to recognize the forehead region.

2. The forehead temperature measurement system as claimed in claim 1, wherein a calibration of calibrating the measured forehead temperature is larger when the forehead area is smaller.

3. The forehead temperature measurement system as claimed in claim 1, wherein a calibration of calibrating the measured forehead temperature is larger when the environment temperature is lower.

4. The forehead temperature measurement system as claimed in claim 1, further comprising a memory configured to previously store a corresponding relationship between the forehead area and the environment temperature as well as calibrations of calibrating the measured forehead temperature for the processor to determine a current calibration according to a current forehead area and a current environment temperature.

5. The forehead temperature measurement system as claimed in claim 4, wherein the corresponding relationship is obtained using a fitting method before shipment and stored in the memory.

6. The forehead temperature measurement system as claimed in claim 1, wherein the first field of view is identical to the second field of view.

7. The forehead temperature measurement system as claimed in claim 1, wherein the measured forehead temperature is a maximum temperature inside the mapped region in the thermal image.

8. The forehead temperature measurement system as claimed in claim 1, wherein the pixel range of the forehead region in the image frame has different sizes and positions in the image frame corresponding to the different distances.

9. A forehead temperature measurement system, configured to measure a forehead temperature of a person at a distance, comprising:

a display;

a substrate;

a lens; and a sensing chip, arranged on the substrate, and comprising:

a first image sensor, comprising a first pixel array having a first number of pixels and having a first field of view configured to cover a face of the person during an operation to receive optical energy from the face via the lens to output a first image frame having the first number of pixels;

a second image sensor;

a first thermal sensor, comprising a second pixel array having a second number of pixels and having a second field of view configured to cover the face of the person during the operation to receive far infrared light from the face via the lens to output a first thermal image having the second number of pixels, which is smaller than the first number of pixels; and a processor, coupled to the first image sensor, the second image sensor and the first thermal sensor, and configured to recognize a first forehead region and calculate a forehead area according to the first image frame, interpolate the first thermal image to cause the second number of pixels to become the first number of pixels to form an interpolated first thermal image, map a pixel range of the first forehead region in the first image frame to the interpolated first thermal image, by overlapping the first number of pixels of the image frame on the first number of pixels of the interpolated first thermal image, to determine a first mapped region, as a determined temperature measuring range of the first thermal sensor, and a measured forehead temperature, determine an environment temperature according to a temperature value of a pixel in the interpolated first thermal image, wherein the pixel is outside and directly adjacent to the first mapped region of the first forehead region when the forehead area is larger than an area threshold, and control the second image sensor to capture a second image frame when a size of the forehead area is smaller than the area threshold to cause the forehead temperature measurement system to be adapted to different distances to compensate for a temperature deviation caused by the distance from the person and environmental temperature fluctuation in a telemetric forehead temperature measurement to prevent false alarm from happening, wherein the first number of pixels is arranged to have a sufficient number to cause the first image frame to contain sufficient details for the processor to recognize the forehead region, and wherein when the forehead area is larger than the area threshold, the processor is further configured to calibrate the measured forehead temperature according to the size of the forehead area and the environment temperature, output a digital value as a flag signal upon the calibrated forehead temperature being higher than a predetermined temperature, and output the calibrated forehead temperature, the display is configured to receive the calibrated forehead temperature and show the received calibrated forehead temperature thereon, and receive the flag signal and generate a warning indicating that a body temperature of the person is too high.

10. The forehead temperature measurement system as claimed in claim 9, wherein a field of view of the second image sensor is smaller than the first field of view of the first image sensor.

11. The forehead temperature measurement system as claimed in claim 9, wherein when the forehead area is larger than the area threshold, the processor is configured to determine the measured forehead temperature according to a temperature value inside the first mapped region.

12. The forehead temperature measurement system as claimed in claim 9, further comprising a second thermal sensor configured to output a second thermal image, wherein a field of view of the second thermal sensor is smaller than the second field of view of the first thermal sensor.

13. The forehead temperature measurement system as claimed in claim 12, wherein when the forehead area is smaller than the area threshold, the processor is further configured to recognize a second forehead region according to the second image frame, map the second forehead region to the second thermal image to determine a second mapped region, and determine the measured forehead temperature according to a temperature value inside the second mapped region.

14. The forehead temperature measurement system as claimed in claim 9, wherein the measured forehead temperature is a maximum temperature in the first mapped region of the interpolated first thermal image.

15. A forehead temperature measurement system, configured to measure a forehead temperature of a person at a distance, comprising:

a display;

a substrate;

a lens; and a sensing chip, arranged on the substrate, and comprising:

a first image sensor, comprising a first pixel array having a first number of pixels and having a first field of view configured to cover a face of the person during an operation to receive optical energy from the face via the lens to output a first image frame having the first number of pixels;

a first thermal sensor, comprising a second pixel array having a second number of pixels and having a second field of view configured to cover the face of the person during the operation to receive far infrared light from the face via the lens to output a first thermal image having the second number of pixels, which is smaller than the first number of pixels; and a processor, coupled to the first image sensor and the first thermal sensor, and configured to recognize a forehead region according to the first image frame, interpolate the first thermal image to cause the second number of pixels to become the first number of pixels to form an interpolated first thermal image, map a pixel range of the forehead region in the first image frame to the interpolated first thermal image, by overlapping the first number of pixels of the image frame on the first number of pixels of the interpolated first thermal image, to determine a mapped region as a determined temperature measuring range of the first thermal sensor, determine an environment temperature according to a temperature value outside the mapped region, find a pixel of interest which has a maximum temperature inside the mapped region, and recognize a ratio of a size of the forehead region in a corresponding region in the first image frame corresponding to a size of the pixel of interest, and calculate a measured forehead temperature according to the maximum temperature, the ratio and the environment temperature when the ratio is lower than a ratio threshold to cause the forehead temperature measurement system to be adapted to different distances to compensate for a temperature deviation caused by the distance from the person and environmental temperature fluctuation in a telemetric forehead temperature measurement to prevent false alarm from happening, wherein when a forehead area is larger than an area threshold, the processor is further configured to calibrate the measured forehead temperature according to a size of the forehead area and the environment temperature, output a digital value as a flag signal upon the calibrated forehead temperature being higher than a predetermined temperature, and output the calibrated forehead temperature, the display is configured to receive the calibrated forehead temperature and show the received calibrated forehead temperature thereon, and receive the flag signal and generate a warning indicating that a body temperature of the person is too high, wherein the environment temperature is a measured temperature value of a pixel in the interpolated first thermal image directly adjacent to the pixel of interest having the maximum temperature, wherein the first number of pixels is arranged to have a sufficient number to cause the first image frame to contain sufficient details for the processor to recognize the forehead region.

16. The forehead temperature measurement system as claimed in claim 15, wherein when the ratio is higher than the ratio threshold, the processor is configured to take the maximum temperature as the measured forehead temperature.

17. The forehead temperature measurement system as claimed in claim 15, further comprising a second image sensor and a second thermal sensor, and the processor is further configured to when the forehead area is smaller than the area threshold, control the second image sensor to capture a second image frame to replace the first image frame and control the second thermal sensor to capture a second thermal image to replace the first thermal image.

18. The forehead temperature measurement system as claimed in claim 17, wherein the first field of view of the first image sensor is identical to the second field of view of the first thermal sensor, and the second image sensor and the second thermal sensor have a field of view smaller than those of the first image sensor and the first thermal sensor.

19. A forehead temperature measurement system, configured to measure a forehead temperature of a person at a distance, comprising:

a substrate;

a lens; and a sensing chip, arranged on the substrate, and comprising:

an image sensor, comprising a first pixel array having a first number of pixels and having a first field of view configured to cover a face of the person during an operation to receive optical energy from the face via the lens to output an image frame having the first number of pixels;

a thermal sensor, comprising a second pixel array having a second number of pixels and having a second field of view configured to cover the face of the person during the operation to receive far infrared light from the face via the lens to output a thermal image having the second number of pixels, which is smaller than the first number of pixels; and a processor, coupled to the image sensor and the thermal sensor, and configured to recognize a forehead region according to the image frame, interpolate the thermal image to cause the second number of pixels to become the first number of pixels to form an interpolated thermal image, map a pixel range of the forehead region in the image frame to the interpolated thermal image, by overlapping the first number of pixels of the image frame on the first number of pixels of the interpolated thermal image, to determine a mapped region as a determined temperature measuring range of the thermal sensor, determine a pixel of interest having a maximum temperature inside the mapped region as a measured forehead temperature, and calibrate the measured forehead temperature according to uniformity of temperature differences between the measured forehead temperature and temperatures of pixels directly adjacent to the pixel of interest in the interpolated thermal image, wherein a calibration value is small in response to high uniformity, and the calibration value is large in response to low uniformity to cause the forehead temperature measurement system to be adapted to different positional relationship with respect to a user to compensate for a temperature deviation caused by the distance from the person and environmental temperature fluctuation in a telemetric forehead temperature measurement to prevent false alarm from happening, output a digital value as a flag signal upon the calibrated forehead temperature being higher than a predetermined temperature, and output the calibrated forehead temperature; and a display, configured to receive the calibrated forehead temperature and show the received calibrated forehead temperature thereon, and receive the flag signal and generate a warning indicating that a body temperature of the person is too high, wherein the uniformity of temperature differences is determined according to a first temperature difference between the maximum temperature and a first adjacent temperature of the maximum temperature as well as a second temperature difference between the maximum temperature and a second adjacent temperature of the maximum temperature, wherein the first number of pixels is arranged to have a sufficient number to cause the image frame to contain sufficient details for the processor to recognize the forehead region.

* * * * *